(12) United States Patent
Woo et al.

(10) Patent No.: US 10,500,242 B2
(45) Date of Patent: Dec. 10, 2019

(54) METHOD OF PRODUCING HIGH-NEPODIN-CONTAINING RUMEX PLANT EXTRACT AND HIGH-NEPODIN-CONTAINING RUMEX PLANT EXTRACT

(71) Applicants: OKINAWA RESEARCH CENTER CO., LTD., Okinawa (JP); UNIVERSITY OF THE RYUKYUS, Okinawa (JP)

(72) Inventors: Je-Tae Woo, Okinawa (JP); Yuto Teruya, Okinawa (JP); Kozue Sasaki, Okinawa (JP); Toshiaki Teruya, Okinawa (JP); Aki Yamano, Okinawa (JP); Kosuke Sueyoshi, Okinawa (JP); Miki Yamada, Okinawa (JP)

(73) Assignees: UNIVERSITY OF THE RYUKYUS, Okinawa (JP); OKINAWA RESEARCH CENTER CO., LTD., Okinawa (JP)

( * ) Notice: Subject to any disclaimer, the term of this patent is extended or adjusted under 35 U.S.C. 154(b) by 0 days.

(21) Appl. No.: 16/089,370

(22) PCT Filed: Feb. 21, 2017

(86) PCT No.: PCT/JP2017/006435
§ 371 (c)(1),
(2) Date: Sep. 28, 2018

(87) PCT Pub. No.: WO2017/169311
PCT Pub. Date: Oct. 5, 2017

(65) Prior Publication Data
US 2019/0105363 A1    Apr. 11, 2019

(30) Foreign Application Priority Data

Mar. 31, 2016   (JP) ................................. 2016-071165

(51) Int. Cl.
*B01D 11/02*    (2006.01)
*A61K 36/70*    (2006.01)
*A61K 31/12*    (2006.01)

(52) U.S. Cl.
CPC .............. *A61K 36/70* (2013.01); *A61K 31/12* (2013.01); *A61K 2236/39* (2013.01)

(58) Field of Classification Search
CPC ................................ B01D 11/02; B01D 11/04
See application file for complete search history.

(56) References Cited

U.S. PATENT DOCUMENTS 8,692,023 B2    4/2014   Yonezawa et al.

FOREIGN PATENT DOCUMENTS

JP    S53-056310    5/1978

OTHER PUBLICATIONS

Notification concerning transmittal of international preliminary report on patentability (Form PCT/IB/326), International preliminary reporton patentability (Form PCT/IB/373) (6 pages).

(Continued)

*Primary Examiner* — Rosanne Kosson
(74) *Attorney, Agent, or Firm* — JMB Davis Ben-David

(57) ABSTRACT

An objective of the present invention is to provide a method for producing a nepodin-containing extract containing a high concentration of nepodin with less contaminants present therein thereby being able to be readily carried out on an industrial scale, when compared to the conventional techniques. The objective is solved by A method for producing a nepodin-containing *Rumex* plant extract, the method comprising the following steps (1) to (5):
(1) a step of subjecting a *Rumex* plant to an extraction treatment using a nepodin-dissolving solvent to obtain a crude *Rumex* plant extract;
(2) a step of subjecting the crude *Rumex* plant extract to a water-adding treatment and/or concentration treatment to obtain a solid crude *Rumex* plant extract;

(Continued)

(3) a step of subjecting the solid crude *Rumex* plant extract to a weak alkali treatment to obtain a weak alkali insoluble product;
(4) a step of subjecting the weak alkali insoluble product to a strong alkali treatment to obtain a strong alkali soluble product; and
(5) a step of subjecting the strong alkali soluble product to a neutralization treatment to obtain the nepodin-containing *Rumex* plant extract.

18 Claims, 1 Drawing Sheet

(56) References Cited

OTHER PUBLICATIONS

Notification of transmittal of translation of the international preliminary report on patentability (Form PCT/IB/338), andTranslation of International preliminary report on patentability (Form PCT/IB/373) (8 pages).
International Search Report ofcorresponding PCT application No. PCT/JP2017/006435.
Tsutomu Odani et al., "Studies on the Antifungal Substance of Crude Drug I : The Root of Rumex japonicus HOUTT." The Japanese Journal of Pharmacognosy, 1977, vol. 31, No. 2, pp. 151 to 154.
Lee, Keyong Ho et al., Archives of Pharmacal Research, 2013, 36(4), pp. 430-435.
Mang, Lan-serng et al., "Chemical constituents of ethyl acetate extract from Rumex hastatus D. Don" Zhongchengyao, 2012, 34(5), pp. 892-895.

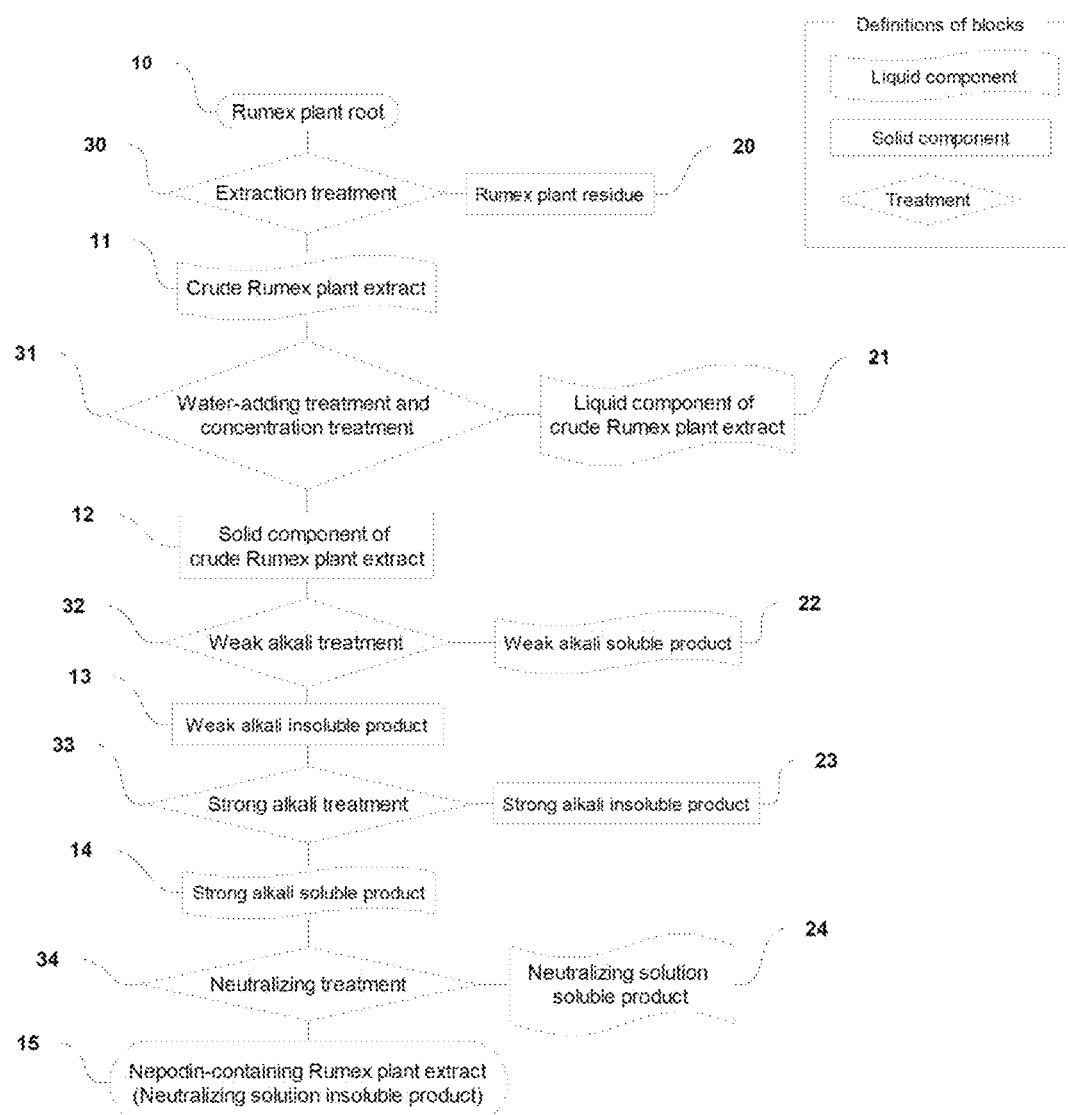

METHOD OF PRODUCING HIGH-NEPODIN-CONTAINING RUMEX PLANT EXTRACT AND HIGH-NEPODIN-CONTAINING RUMEX PLANT EXTRACT

CROSS-REFERENCE TO RELATED APPLICATION

This is the U.S. National Stage of International Patent Application No. PCT/JP2017/006435 filed on Feb. 21, 2017, which was published in Japanese, and which claims the benefit of priority to Japanese Patent Application No. 2016-071165 filed on Mar. 31, 2016, the disclosure of which is incorporated herein by reference in its entirety.

TECHNICAL FIELD

The present invention relates to a method for producing an extract of *Rumex* plants containing a high concentration of nepodin as well as to such an extract.

BACKGROUND ART

Nepodin (CAS: 3785-24-8), also referred to as musizin and dianellidin, has a structure represented by the formula (1) given below. It is known that nepodin has pharmacological activities to improve various conditions, including glucose tolerance and blood lipid levels and to ameliorate metabolic syndromes, by activating 5'-adenosine monophosphate-activated protein kinase (AMPK) (See, for example, Non-Patent Document 1 below, the entire disclosure of which is incorporated herein by reference).

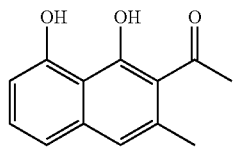

(Chemiucal formula 1)

*Rumex* plants, perennial plants of the genus *Rumex* of the family Polygonaceae, are known as a natural material containing nepodin. Among known *Rumex* species are *R. japonicus, R. crispus, R. obtusifolius* and *R. maritimus*.

In a known technique to obtain nepodin from *Rumex* plants, plant parts such as roots and stems are subjected to an extraction process using organic solvents that can dissolve nepodin, such as ethanol and ethyl acetate (See, Non-Patent Documents 1 and 2 below, the entire disclosure of which is incorporated herein by reference).

PRIOR ART DOCUMENT

Patent Document

Patent Document 1: JP 5727481 B

Non-Patent Document

Non-Patent Document 1: Lee, Keyong Ho et al., Archives of Pharmacal Research, 2013, 36(4), pp. 430-435
Non-Patent Document 2: Zhang, Lan-serng et al., Zhongchengyao, 2012, 34(5), pp. 892-895

SUMMARY OF INVENTION

Problems to be Solved by the Invention

Because nepodin present in *Rumex* plants has a number of pharmacological activities as described in Patent Document 1, there is an increasing demand to use nepodin as an active ingredient in pharmaceutical products and quasi-pharmaceutical products. Thus, if a technique becomes available that enables efficient production of extracts of natural materials containing nepodin (referred to as "nepodin-containing extracts," hereinafter), nepodin-containing extracts are further expected to be employed as an active ingredient or an additive in pharmaceutical products and other products.

However, while the techniques described in Non-Patent Documents 1 and 2 may provide nepodin-containing extracts, the resulting nepodin-containing extracts undesirably contain significant amounts of fatty acids and other contaminants derived from *Rumex* plants. Furthermore, the resulting nepodin-containing extracts need to be subjected to a concentration process in order to obtain products containing a high concentration of nepodin. Such a concentration process requires a large-scale facility and can be time-consuming depending on the amounts of the extraction solvents and is thus difficult to carry out on an industrial scale.

Accordingly, it is an objective of the present invention to provide a method for producing a nepodin-containing extract containing a high concentration of nepodin with less contaminants present therein thereby being able to be readily carried out on an industrial scale, when compared to the above conventional techniques.

Means of Solving the Problems

In an effort to find solutions to the above-described problems, the present inventors have found that a solid product containing nepodin can be obtained by subjecting *Rumex* plants to an extraction treatment to obtain a crude extract of *Rumex* plants, and subsequently subjecting the crude extract to a water-adding and/or concentration treatment. The solid product was further treated sequentially with a weak alkali and then with a strong alkali to obtain an aqueous solution containing nepodin, and the aqueous solution was then subjected to a neutralizing treatment. In this manner, the present inventors have ultimately succeeded in producing a nepodin-containing extract of *Rumex* plants that contains as high as 20 wt % to 40 wt % of nepodin while containing less contaminants derived from *Rumex* plants such as fatty acids. The present invention has been completed based on these findings and successful examples.

According to one aspect of the present invention, there is provided a method for producing a nepodin-containing *Rumex* plant extract, the method comprising the following steps (1) to (5):

(1) a step of subjecting a *Rumex* plant to an extraction treatment using a nepodin-dissolving solvent to obtain a crude *Rumex* plant extract;

(2) a step of subjecting the crude *Rumex* plant extract to a water-adding treatment and/or concentration treatment to obtain a solid crude *Rumex* plant extract;

(3) a step of subjecting the solid crude *Rumex* plant extract to a weak alkali treatment to obtain a weak alkali insoluble product;

(4) a step of subjecting the weak alkali insoluble product to a strong alkali treatment to obtain a strong alkali soluble product; and (5) a step of subjecting the strong alkali soluble product to a neutralization treatment to obtain the nepodin-containing *Rumex* plant extract.

Preferably, in the production method in one embodiment of the present invention, the nepodin-dissolving solvent is 20% to 100% (v/v) ethanol.

Preferably, in the production method in one embodiment of the present invention, the weak alkali treatment is a weak alkali treatment using a weak alkaline aqueous solution having a pH of 8 to 10.

Preferably, in the production method in one embodiment of the present invention, the weak alkali treatment is a weak alkali treatment using a weak alkaline aqueous solution obtained by mixing sodium bicarbonate and water, and having a pH of 8 to 10.

Preferably, in the production method in one embodiment of the present invention, the strong alkali treatment is a strong alkali treatment using a strong alkaline aqueous solution having a pH of 12 to 14.

Preferably, in the production method in one embodiment of the present invention, the strong alkali treatment is a strong alkali treatment using a strong alkaline aqueous solution obtained by mixing sodium hydroxide and water, and having a pH of 12 to 14.

Preferably, in the production method in one embodiment of the present invention, the neutralizing treatment is a neutralizing treatment using an acidic aqueous solution having a pH of 1 to 3.

Preferably, in the production method in one embodiment of the present invention, the neutralizing treatment is a neutralizing treatment using an acidic aqueous solution obtained by mixing water and an acid component selected from the group consisting of acetic acid, and hydrochloric acid and having a pH of 1 to 3.

Preferably, in the production method in one embodiment of the present invention, the nepodin-containing *Rumex* plant extract is a nepodin-containing *Rumex* plant extract containing 20 wt % to 40 wt % of nepodin.

According to one aspect of the present invention, there is provided a nepodin-containing *Rumex* plant extract containing 20 wt % to 40 wt % nepodin and 60 wt % or less fatty acids.

Preferably, in the nepodin-containing *Rumex* plant extract in one embodiment of the present invention, the nepodin-containing *Rumex* plant extract is a nepodin-containing *Rumex* plant extract obtained by the production method in one embodiment of the present invention.

Advantageous Effects of the Invention

According to the production method in one embodiment of the present invention, nepodin-containing *Rumex* plant extracts containing a high concentration of nepodin with less contaminants derived from *Rumex* plants can be produced in a manner that can be readily implemented on an industrial scale as compared to any of conventional techniques since the principle of production method is based on addition of solutions and solid/liquid separation and since the method involves only simple steps.

According to the nepodin-containing *Rumex* plant extracts in one embodiment of the present invention, various pharmaceutical products and quasi-pharmaceutical products containing as an active ingredient not only nepodin-containing *Rumex* plant extracts themselves but also purified nepodin obtained by purifying nepodin-containing *Rumex* plant extracts can be produced. In this regard, the nepodin-containing *Rumex* plant extracts and the purified nepodin may be used either alone or in combination with other additives in powders, granules, tablets, solutions, pastes, capsules, gels and various other forms for use as pharmaceutical products or quasi-pharmaceutical products.

BRIEF DESCRIPTION OF DRAWINGS

FIG. 1 is a flowchart schematically illustrating a production method in one embodiment of the present invention.

DETAILED DESCRIPTION OF THE INVENTION

Modes for Carrying Out the Invention

The present invention will now be described in further details.

The production method in one embodiment of the present invention relates to a method for producing an extract of *Rumex* plants containing a high concentration of nepodin by subjecting a solid crude extract of *Rumex* plants to a weak alkali treatment, a strong alkali treatment, and a neutralizing treatment. A first embodiment of the present invention includes at least the following steps (1) to (5):

(1) a step of subjecting a *Rumex* plant to an extraction treatment using a nepodin-dissolving solvent to obtain a crude *Rumex* plant extract;

(2) a step of subjecting the crude *Rumex* plant extract to a water-adding treatment and/or concentration treatment to obtain a solid crude *Rumex* plant extract;

(3) a step of subjecting the solid crude *Rumex* plant extract to a weak alkali treatment to obtain a weak alkali insoluble product;

(4) a step of subjecting the weak alkali insoluble product to a strong alkali treatment to obtain a strong alkali soluble product; and (5) a step of subjecting the strong alkali soluble product to a neutralization treatment to obtain the nepodin-containing *Rumex* plant extract.

Docks and sorrels, or *Rumex* plants (gishi-gishi), as used herein are commonly known plants forming a genus in the family Polygonaceae. They are perennial plants, and certain species are widely distributed throughout Japan. *Rumex* plants are known as weeds commonly found growing on roadside and alleys in rice fields. It is also known that *Rumex* plants grow stems length of which is about one meter long in early summer, and bear flowers resembling buckwheat flowers in clusters. *Rumex* plants include, but are not limited to, any *Rumex* plant containing nepodin, including for example, *Rumex japonicus* (gishi-gishi), *R. crispus*, *R. obtusifolius*, *R. gmelini*, *R. nepalensis*, *R. hastatus*, *R. alpinus*, *R. acetosa*, *R. cripus*, *R. stenophyllus*, *R. patientia*, *R. chalepensis* and *R. orientalis*.

*Rumex* plants also include any plant closely related to *Rumex* plants and containing nepodin. Examples of plants closely related to *Rumex* plants include, but are not limited to, *Dianella ensifolia*, *D. revoluta*, *D. callicarpa*, and *D. nigra*, each closely related to family Polygonaceae; *Hemerocallis minor*; *Simethis bicolor Kunth* of family Agavaceae; *Limonium myrianthum* of genus *Limonium* of family Plumbaginaceae; *Rhamnus prinoides*, *R. wightii*, and *R. procumbens*, each belonging to genus Rhamnaceae; *Myrsine africana* of genus *Myrsine* of family Myrsinaceae; and other plants such as *Maesopsis eminii*.

The *Rumex* plant may be one or two or more of the above-described plants of family Polygonaceae and the plants closely related to family Polygonaceae, or any of crossbreeds of the plants listed above as specific examples.

While the part of *Rumex* plant used is not particularly limited as long as the part is a plant part that contains nepodin, roots are preferred as they contain high contents of nepodin per unit mass. In addition to roots, the *Rumex* plant may be a mixture of stems, leaves, flowers and other plant parts.

Specific examples of *Rumex* plants include roots of *Rumex japonicus, Rumex gmelinii, Rumex crispus, Rumex andreaeanus Makino, Rumex obtusifolius, R. hastatus, D. ensifolia, D. callicarpa* (Liliaceae), *D. nigra, Hemerocallis flava* and *Myrsine africana*; leaves of *R. prinoides*; and tree barks of *R. wightii*. Of these, roots of *Rumex japonicus* are known as "Youtei" and have been historically used as herbal drugs and are thus preferred. It is known that in addition to nepodin, the roots of *Rumex* plants contain chrysophanol, emodin, chrysophanolanthrone and oxalic acid and have anti-microbial and anti-coagulant activities.

Preferably, *Rumex* plants are subjected to the production method in one embodiment of the present invention immediately after they are harvested. When *Rumex* plants are not subject to the production method immediately, they are preferably stored by using storage means commonly used by those skilled in the art, such as cold storage, in order to prevent *Rumex* plants from being denatured.

The harvested *Rumex* plants may be subjected to various pre-treatments including drying treatment, grinding treatment, fragmentation treatment, and combination thereof.

For example, drying treatment and grinding treatment may be combined to form *Rumex* plants into dry powder. To this end, the drying treatment and the grinding treatment may be carried out simultaneously or one treatment may be carried out before the other treatment. The drying treatment preferably precedes the grinding treatment in view of easier working.

The drying treatment is not limited to any particular treatment. The drying treatment may include a treatment of drying *Rumex* plants in such a manner that the water content of the *Rumex* plants would become 10 wt % or less, preferably 5 wt % or less. For example, the drying treatment may be carried out by sun drying, or by using a dryer to perform hot air stream drying, warm air stream drying, high-pressure vapor drying, spray drying, vacuum drying, flow drying, electromagnetic wave drying and freeze-drying, and other drying treatments known to those skilled in the art. Drying by heating may be carried out at a temperature over a period of time such that *Rumex* plants or nepodin is not denatured due to heating; for example, it may be carried out at 30° C. to 140° C., preferably at 40° C. to 100° C.

While the grinding treatment is not limited to any particular treatment, it may include a treatment of grinding plant bodies by using any technique commonly used by those skilled in the art with a device or tool designed for grinding, such as crusher, mill, blender and grindstone. While the fragmentation treatment is not limited to any particular treatment, it may be carried out by using a technique commonly used by those skilled in the art for fragmenting plant bodies, such as slicing, crushing and shredding.

In Step (1) of the production method in one embodiment of the present invention, the *Rumex* plant immediately after harvesting or subjected to the storage or pre-treatment after harvesting is subjected to an extraction treatment using a nepodin-dissolving solvent to obtain a crude *Rumex* plant extract.

The nepodin-dissolving solvent is not particularly limited as long as it is any solvent that can dissolve nepodin. The nepodin-dissolving solvent includes, for example, solvents that can readily dissolve nepodin, specifically organic solvents such as ethanol and ethyl acetate, and solvent mixtures of these organic solvents and water. When the nepodin-dissolving solvent is a solvent mixture of ethanol and water, the solvent mixture is preferably 20% to 100% (v/v) ethanol. The solvent mixture with the ethanol concentration less than 20% (v/v) may have decreased extraction efficiency. When safety and possibility of industrialization are considered in addition to the extraction efficiency, the nepodin-dissolving solvent is preferably 20% to 80% (v/v) ethanol, more preferably 20% to 60% (v/v) ethanol.

The condition for the extraction treatment is not particularly limited as long as it is any suitable condition that allows nepodin in *Rumex* plants to dissolve in the solvent. Such a condition may be suitably determined depending on the state and the amount of *Rumex* plant used as well as the type and the amount of the nepodin-dissolving solvent used. The condition for the extraction treatment may be determined by properly sampling the treatment solution obtained from the *Rumex* plant with the nepodin-dissolving solvent to monitor the concentration of nepodin in the treatment solution.

Specifically, the extraction treatment may be carried out by using 2 times to 20 times by mass of 20% to 100% (v/v) ethanol with respect the *Rumex* plant at 10° C. to 80° C., preferably at room temperature to 60° C. for several hours to several days, although the extraction treatment may be carried out under other conditions. While the recovery rate of nepodin in the nepodin extract is not particularly limited, 50% or more nepodin is preferably recovered based on the estimated content of nepodin present in the *Rumex* plant material.

The crude *Rumex* plant extract obtained in Step (1) contains a certain amount of a solid component resulting from the *Rumex* plant. In terms of the treatment efficiency of the subsequent Step (2), it is preferred that the crude *Rumex* plant extract obtained in Step (1) is subjected to a commonly known solid/liquid separation means, such as centrifugation and filtration, to remove the residues of the *Rumex* plant and form a liquid component.

In Step (2) of the production method in one embodiment of the present invention, the crude *Rumex* plant extract obtained in Step (1) is subjected to a water-adding treatment, a concentration treatment, or a water-adding treatment and a concentration treatment to obtain a solid crude *Rumex* plant extract.

The water-adding treatment is not limited to any particular treatment as long as water is added to the crude *Rumex* plant extract so that the solid component in the crude *Rumex* plant extract can appear. For example, the water-adding treatment may be carried out by bringing 0.1 times to 5 times, preferably 0.2 times to 0.8 times as much water as the crude *Rumex* extract into contact with the crude *Rumex* extract and leaving or stirring the water-added crude *Rumex* extract at 10 to 30° C., preferably at room temperature, for several minutes to several hours to several days.

The concentration treatment is not limited to any particular treatment as long as it is a treatment of concentrating the crude *Rumex* plant extract under the condition such that the solid component in the crude *Rumex* plant extract can appear by commonly known concentration means. For example, the concentration treatment may be carried out by leaving the crude *Rumex* plant extract under a reduced pressure or low temperature for several minutes to several hours to several days to allow the liquid component in the crude *Rumex* plant extract to evaporate. While the degree of concentration is not particularly limited, the crude *Rumex* plant extract may be concentrated to about ½ to about 1/10 by volume or the liquid component may be evaporated until the crude *Rumex* plant extract becomes a dry solid.

Either one or both of the water-adding treatment and the concentration treatment may be carried out. While the order and the number of times of the water-adding treatment and the concentration treatment are not particularly limited, the water-adding treatment may precede the concentration treatment. The solid crude *Rumex* plant extract obtained by the water-adding treatment and/or the concentration treatment can be used in the subsequent step either directly or as a solid component obtained by subjecting the solid crude *Rumex* plant extract to a commonly known solid/liquid separation means such as centrifugation and filtration. The solid crude *Rumex* plant extract may be subjected to the above-described drying treatment or the grinding treatment or the other treatments.

While the concentration (i.e., content) of nepodin in the solid crude *Rumex* plant extract is not particularly limited, for example, it may be 10 wt % or more, preferably 15 wt % or more based on the wet mass of the solid crude *Rumex* plant extract.

In Step (3) of the production treatment in one embodiment of the present invention, the solid crude *Rumex* plant extract obtained by Step (2) is subjected to a weak alkali treatment to obtain a weak alkali insoluble product as an insoluble nepodin-containing component.

The weak alkali treatment of the solid crude *Rumex* plant extract can remove fatty acids and other contaminants present in the solid crude *Rumex* plant extract to form a weak alkali insoluble product containing a high concentration of nepodin.

The weak alkali is not limited to any particular weak alkali as long as it can degrade the contaminants in the solid crude *Rumex* plant extract and as long as it does not dissolve nepodin. For example, the weak alkali is preferably a solution formed by dissolving a weak alkali component such as sodium bicarbonate, aqueous ammonia, sodium carbonate, calcium carbonate, magnesium carbonate and magnesium oxide in a solvent that does not dissolve nepodin, such as water, and having its pH adjusted to 7.5 to 11, preferably 8 to 10. More preferably, the weak alkali is an aqueous sodium bicarbonate solution having its pH adjusted to 8 to 10. The concentration of the weak alkali component used is not particularly limited as long as a predetermined pH is achieved. For example, if used, the aqueous sodium bicarbonate solution is preferably a 0.01% to 10% (w/v) aqueous sodium bicarbonate solution and more preferably a 0.05% to 0.5% (w/v) aqueous sodium bicarbonate solution.

The weak alkali treatment is not particularly limited and may be carried out under any condition as long as the contaminants present in the solid crude *Rumex* plant extract are degraded and nepodin is precipitated as an insoluble component. For example, the solid crude *Rumex* plant extract may be brought into contact with the weak alkali solution and the mixture may be left at 10° C. to 30° C., preferably at room temperature, for several minutes to several hours to several days until a suspension forms. To obtain the suspension in a shorter period of time, the mixture of the solid crude *Rumex* plant extract and the weak alkali may be subjected to a commonly known means for forming a suspension, such as stirring and ultrasonication.

The weak alkali insoluble product obtained by the weak alkali treatment is used in the subsequent step in a form with its liquid component removed, for example, as a solid component obtained by subjecting the weak alkali insoluble product to a commonly known solid/liquid separation means such as centrifugation and filtration. The weak alkali insoluble product may be subjected to the above-described drying treatment or the grinding treatment or the other treatments.

In Step (4) of the production treatment in one embodiment of the present invention, the weak alkali insoluble product obtained by Step (3) is subjected to a strong alkali treatment to obtain a strong alkali soluble product as a soluble nepodin-containing component.

The strong alkali treatment of the weak alkali insoluble product can dissolve nepodin present in the weak alkali insoluble product to form a strong alkali soluble product containing a high concentration of nepodin. The weak alkali insoluble product tends to contain fatty acids and anthraquinones.

The strong alkali is not limited to any particular strong alkali as long as it can dissolve nepodin present in the weak alkali insoluble product. For example, the strong alkali is preferably a solution formed by dissolving a strong alkali component such as sodium hydroxide, potassium hydroxide and calcium hydroxide in a solvent such as water, and having its pH adjusted to 11.5 to 14, preferably 12 to 14. More preferably, the strong alkali is an aqueous sodium hydroxide solution having its pH adjusted to 12 to 14. The concentration of the strong alkali component used is not particularly limited as long as a predetermined pH is achieved. For example, if used, the aqueous sodium hydroxide solution is preferably a 0.01% to 10% (w/v) aqueous sodium hydroxide solution and more preferably a 0.05% to 0.5% (w/v) aqueous sodium hydroxide solution.

The strong alkali treatment is not particularly limited and may be carried out under any condition as long as nepodin present in the weak alkali insoluble product is dissolved and a strong alkali soluble product is obtained as a nepodin-containing component. For example, the weak alkali insoluble product may be brought into contact with the strong alkali solution and the mixture may be left at 10° C. to 30° C., preferably at room temperature, for several minutes to several hours. To obtain the strong alkali soluble product in a shorter period of time, the mixture of the weak alkali insoluble product and the strong alkali may be subjected to a commonly known dissolving means, such as stirring and ultrasonication.

The strong alkali soluble product obtained by the strong alkali treatment is used in the subsequent step in a form with its solid component removed, for example, as a liquid component obtained by subjecting the strong alkali soluble product to a commonly known solid/liquid separation means such as centrifugation and filtration.

In Step (5) of the production treatment in one embodiment of the present invention, the strong alkali soluble product obtained by Step (4) is subjected to a neutralizing treatment and neutralized to obtain a nepodin-containing *Rumex* plant extract as a solid component insoluble in a neutral solution.

For example, the neutralizing treatment may be carried out by using an acid that can adjust the strong alkali soluble product to a near-neutral pH, preferably to a pH of about 6 to 8. The acid is not particularly limited as long as it is any acid commonly used in a neutralizing treatment. The acid includes, for example, inorganic acids and organic acids such as acetic acid, hydrochloric acid, formic acid, sulfuric acid and phosphoric acid. The acid is preferably acetic acid or hydrochloric acid having a pH of 1 to 3. The acid may be a mixture with a nepodin-insoluble solvent such as water.

The neutralizing treatment is not particularly limited and may be carried out under any condition as long as the strong alkali soluble product is neutralized and nepodin is precipitated as an insoluble component. For example, the strong alkali soluble product may be brought into contact with the acid and the mixture may be left at 10° C. to 30° C., preferably at room temperature, for several minutes to several hours to several days until a suspension forms. To obtain the suspension in a shorter period of time, the mixture of the strong alkali soluble product and the acid may be subjected to a commonly known means for forming a suspension, such as stirring and ultrasonication.

The nepodin-containing *Rumex* plant extract obtained by the neutralizing treatment is preferably obtained in a form with its liquid component removed, for example, as a solid component obtained by subjecting the strong alkali soluble product to a commonly known solid/liquid separation means such as centrifugation and filtration.

For example, when the nepodin-containing *Rumex* plant extract is used as a raw material to make an oral composition or external composition, it is preferably washed with water or the like. Optionally, the nepodin-containing *Rumex* plant extract may be subjected to a purification treatment. For example, a mixture of the collected and water-washed nepodin-containing *Rumex* plant extract and the nepodin-dissolving solvent can be subjected to a solid/liquid separation treatment to obtain a nepodin-containing *Rumex* plant extract with reduced impurities as a liquid component.

The nepodin-containing *Rumex* plant extract obtained by the production method in one embodiment of the present invention is a composition derived from *Rumex* plant and containing a higher concentration of nepodin as compared to the extracts obtained by any of the conventional methods. While the concentration (i.e., content) of nepodin in the nepodin-containing *Rumex* plant extract is not particularly limited, it is for example 20 wt % or more, preferably 30 wt % or more, more preferably 40 wt % or more based on the dry mass of the nepodin-containing *Rumex* plant extract. Furthermore, the recovery rate of nepodin in the nepodin-containing *Rumex* plant extract is for example 40% or more, preferably 50% or more, more preferably 60% or more based on the amount of nepodin present in the solid crude *Rumex* plant extract.

The amount of fatty acids or complexes thereof in the nepodin-containing extract is preferably 60 wt % or less, more preferably 40 wt % or less, and still more preferably about 30 wt % or less. The nepodin-containing extract may also contain by-products: it may contain nakahalene, a nepodin analog, in an amount of about 1 to about 15 wt %, preferably 10 wt % or less, and emodin, chrysophanol and physcion, each an anthraquinone, in an amount of about 1 to about 10 wt %, preferably 8 wt % or less.

The production method in one embodiment of the present invention may include various other steps or operations before, after, or during the above-described steps as long as the objectives of the present invention can be achieved.

A specific embodiment of the production method in one embodiment of the present invention will now be described with reference to FIG. 1, which depicts an exemplary method for producing a *Rumex* plant extract containing a high concentration of nepodin using the root of the *Rumex* plant as the starting material. However, the production method in one embodiment of the present invention is not limited to the method described below.

The roots of *Rumex* plants are dug up when the scapes die down (during July to September) and are stripped of rootlets. The roots are thoroughly dried in the sun. The dried *Rumex* plant root 10 is ground and a predetermined amount of the dried root is weighed. Two to ten times by mass of ethanol with respect to the root of *Rumex* plant is then added to the weighed root and the root is left to stand for 5 hours to 15 hours at room temperature to carry out an extraction treatment 30. Subsequently, *Rumex* plant residue 20 is removed by a solid/liquid separation means to obtain a crude *Rumex* plant extract 11.

To the resulting crude *Rumex* plant extract 11, 0.2 times to 0.5 times of water with respect to the crude *Rumex* plant extract 11 is added and the crude extract is concentrated under reduced pressure, thereby carrying out a water-adding treatment and concentration treatment 31. The liquid component of the crude *Rumex* plant extract 21 is then removed by a solid/liquid separation means to obtain a solid component of crude *Rumex* plant extract 12. Instead of carrying out the water-adding treatment and concentration treatment 31, only the water-adding treatment or the concentration treatment may be carried out.

Subsequently, the resulting solid component of crude *Rumex* plant extract is subjected to a weak alkali treatment 32 using a 0.05% to 1% (w/v) aqueous weak alkali solution (pH=8 to 10). The weak alkali insoluble product 22 is removed by a solid/liquid separation means to obtain a weak alkali insoluble product 13.

Subsequently, the resulting weak alkali insoluble product 13 is subjected to a strong alkali treatment 33 using a 0.05% to 1% (w/v) aqueous strong alkali solution (pH=12 to 14). The strong alkali insoluble product 23 is removed by a solid/liquid separation means to obtain a strong alkali soluble product 14.

Subsequently, the resulting strong alkali soluble product 14 is subjected to a neutralizing treatment 34 using an acid (pH=1 to 3) so that a pH of the solution becomes 7 to 8. The neutralizing solution soluble product 24 is removed by a solid/liquid separation means to obtain a nepodin-containing *Rumex* plant extract 15.

The nepodin-containing *Rumex* plant extract produced by the production method in one embodiment of the present invention may be encompassed by the present invention as another embodiment. The nepodin-containing *Rumex* plant extract in one embodiment of the present invention is not particularly limited as long as it is produced using the production method in one embodiment of the present invention and it contains a higher concentration of nepodin as compared to extracts obtained by any of the conventional methods. For example, the nepodin content in the nepodin-containing *Rumex* plant extract based on the dry weight of the extract is preferably 20 wt % or more, more preferably 30 wt % or more, and still more preferably 40 wt % or more in terms of the production cost in the case where the extract is employed as a material for oral composition or external composition.

Applications of the nepodin-containing *Rumex* plant extract in one embodiment of the present invention are not particularly limited: for example, the nepodin-containing *Rumex* plant extract may be used as a material of composition or as composition per se in oral compositions, such as food and beverage products and pharmaceutical products, as well as in external compositions, such as cosmetic products, where it is expected to provide pharmacological activities of nepodin to improve various conditions, including glucose tolerance and blood lipid levels and to ameliorate metabolic syndromes, by activating AMPK. The nepodin content of the nepodin-containing *Rumex* plant extract in one embodiment of the present invention can be determined by the method described in Examples below.

The present invention will now be described in further detail with reference to the following Examples, which are not intended to limit the present invention. The present invention may take various forms to the extent that the objectives of the present invention are achieved.

EXAMPLES

Example 1: Method for Determining Nepodin

The nepodin content (mg) was determined by using a COSMOSIL 5C18-AR-2 column with a mobile phase of MeOH: $H_2O$=70:30 with 0.1% TFA at flow rate of 1 ml/min and detection wavelength of 225.0 nm. The nepodin was detected as a peak at retention time of about 11 to 12 min and quantified by calibration curve analysis.

Example 2: Production Method (1) for High-Nepodin-Containing Extract of Raw Root of Rumex Plant To 2.5 L of ethanol, 500 g of the raw root of Rumex plant (R. japonicus) was added and the mixture was left to stand for 9 hours at room temperature to obtain a crude Rumex plant root extract. The resulting crude Rumex plant extract was suction-filtrated through paper filter to obtain a crude Rumex plant root extract liquor. The concentration of nepodin in a concentrate of the Rumex plant root extract liquor obtained by concentrating some of the crude Rumex plant root extract liquor under reduced pressure was 2.8 wt %.

1.0 L of water was added to 2.5 L of the crude Rumex plant root extract liquor and ethanol was removed by concentration under reduced pressure to precipitate a water insoluble product. The precipitated water insoluble product was separated and collected by centrifugation (40×100 rpm, 10 min) to obtain 3.0 g (wet weight) of the water insoluble product. The concentration of nepodin in the wet water insoluble product was 18.8 wt %.

101.1 mg of the wet water insoluble product was added and suspended in 15 ml of a 0.1% (w/v) aqueous sodium bicarbonate solution by ultrasonication. The resulting suspension was separated by centrifugation (40×100 rpm, 10 min) into a supernatant (1) containing a weak alkali soluble product and a precipitate (1) containing a weak alkali insoluble product. To the resulting precipitate (1), 15 ml of a 0.1% (w/v) aqueous sodium hydroxide solution was added and the mixture was subjected to stirring treatment for 1 hour and then separated by centrifugation (40×100 rpm, 10 min) into a supernatant (2) containing a strong alkali soluble product and a precipitate (2) containing a strong alkali insoluble product. To the resulting supernatant (2), 1 mL of acetic acid was added and the mixture was gently agitated to cause the solid component to precipitate, followed by separation by centrifugation (40×100 rpm, 20 min) into a supernatant (3) containing an acid soluble product and a precipitate (3) containing an acid insoluble product. The amount of nepodin present in 25.8 mg of the resulting precipitate (3) was 13.1 mg and the concentration of nepodin based on the dry weight of the precipitate (3) was 50.8 wt %.

Consequently, a high-nepodin-containing extract of Rumex plant root containing 50.8 wt % of nepodin was obtained as a final product. Since 19 mg of nepodin was contained in 101.1 mg of the wet water insoluble product (nepodin concentration of 18.8 wt %), 68.9% of nepodin was recovered in the final product of high-nepodin-containing Rumex plant root extract with respect to the intermediate wet water insoluble product.

Example 3: Production Method (2) for High-Nepodin-Containing Extract of Raw Root of Rumex Plant To 1 L of ethanol, 500 g of the raw root of Rumex plant (R. japonicus) was added and the mixture was left to stand for 8 hours at room temperature to obtain a crude Rumex plant root extract. The resulting crude Rumex plant root extract was suction-filtrated using a diaphragm pump and a filtration flask to obtain a crude Rumex plant root extract liquor.

The crude Rumex plant root extract liquor was concentrated down to about 200 mL under reduced pressure to cause the solid component to precipitate. The precipitated solid component was separated and collected by centrifugation (4,500 rpm, 30 min).

The resulting solid component was added to 150 ml of a 0.1% (w/v) aqueous sodium bicarbonate solution and the mixture was stirred to obtain a suspension. The resulting suspension was separated by centrifugation (4,000 rpm, 10 min) into a supernatant (1) and a precipitate (1). The resulting precipitate (1) was added to 150 ml of a 0.1% (w/v) aqueous sodium hydroxide solution and the mixture was stirred. Subsequently, the mixture was separated by centrifugation (4,000 rpm, 30 min) into a supernatant (2) and a precipitate (2). To the resulting supernatant (2), a suitable amount of acetic acid was added with the aim of neutralization to cause the solid component to precipitate, followed by separation by centrifugation (4,000 rpm, 10 min) into a supernatant (3) and a precipitate (3). The resulting precipitate (3) was dried and the amount of the dried product of the precipitate (3) was determined to be 556 mg. The concentration of nepodin in the dried product of the precipitate (3) was 41.4 wt %.

Consequently, a high-nepodin-containing extract of Rumex plant root containing 41.4 wt % of nepodin was obtained as a final product.

Example 4: Production Method (3) for High-Nepodin-Containing Extract of Raw Root of Rumex Plant To 1 L of ethanol, 500 g of the raw root of Rumex plant (R. obtusifolius) was added and the mixture was left to stand for 8 hours at room temperature to obtain a crude Rumex plant root extract. The resulting crude Rumex plant root extract was suction-filtrated using a diaphragm pump and a filtration flask to obtain a crude Rumex plant root extract liquor.

500 mL of water was added to the crude Rumex plant root extract liquor and the solution was concentrated down to about 300 mL under reduced pressure to cause the solid component to precipitate. The precipitated solid component was separated and collected by centrifugation (7,500 rpm, 10 min).

The resulting solid component was added to 100 ml of a 0.1% (w/v) aqueous sodium bicarbonate solution and the mixture was stirred to obtain a suspension. The resulting suspension was separated by centrifugation (7, 500 rpm, 10 min) into a supernatant (1) and a precipitate (1). The resulting precipitate (1) was added to 200 ml of a 0.1% (w/v) aqueous sodium hydroxide solution and the mixture was stirred. Subsequently, the mixture was separated by centrifugation (7,500 rpm, 10 min) into a supernatant (2) and a precipitate (2). To the resulting supernatant (2), a suitable amount of acetic acid was added with the aim of neutralization to cause the solid component to precipitate, followed by separation by centrifugation (7,500 rpm, 10 min) into a supernatant (3) and a precipitate (3). The resulting precipitate (3) was dried and the amount of the dried product of the precipitate (3) was determined to be 241.3 mg. The concentration of nepodin in the dried product of the precipitate (3) was 40.5 wt %. The results are shown in Table 1.

TABLE 1

|  | Mass of extract | Concentration of nepodin contained | Amount of nepodin contained |
|---|---|---|---|
| Crude Rumex plant root extract liquor | 19.22 g* | 1.7 wt % | 334.5 mg |
| Precipitate (3) | 241.3 mg | 40.5 wt % | 97.7 mg |

*The weight of the crude Rumex plant root extract liquor of R. obtusifolius was calculated by concentrating a portion of the solution.

Consequently, a high-nepodin-containing extract of Rumex plant root containing 40.5 wt % of nepodin was obtained as a final product.

Example 5: Production Method (1) for High-Nepodin-Containing Extract of Dried Root of Rumex Plant The root of Rumex plant (R. obtusifolius) was dried by hot air stream at 40° C. for 8 hours to obtain a dried root of R. obtusifolius. To 1 L of ethanol, 170 g of the dried root of R. obtusifolius was then added and the mixture was left to stand for 8 hours at room temperature to obtain a crude Rumex plant root extract. The resulting crude Rumex plant root extract was suction-filtered using a diaphragm pump and a filtration flask to obtain a crude Rumex plant root extract liquor.

500 mL of water was added to the crude Rumex plant root extract liquor and the solution was concentrated down to about 300 mL under reduced pressure to cause the solid component to precipitate. The precipitated solid component was separated and collected by centrifugation (7,500 rpm, 10 min).

The resulting solid component was added to 100 ml of a 0.1% (w/v) aqueous sodium bicarbonate solution and the mixture was stirred to obtain a suspension. The resulting suspension was separated by centrifugation (7, 500 rpm, 10 min) into a supernatant (1) and a precipitate (1). The resulting precipitate (1) was added to 200 ml of a 0.1% (w/v) aqueous sodium hydroxide solution and the mixture was stirred. Subsequently, the mixture was separated by centrifugation (7,500 rpm, 10 min) into a supernatant (2) and a precipitate (2). To the resulting supernatant (2), a suitable amount of acetic acid was added with the aim of neutralization to cause the solid component to precipitate, followed by separation by centrifugation (7,500 rpm, 10 min) into a supernatant (3) and a precipitate (3). The resulting precipitate (3) was dried and the amount of the dried product of the precipitate (3) was determined to be 128.4 mg. The concentration of nepodin in the dried product of the precipitate (3) was 22.7 wt %. The results are shown in Table 2.

TABLE 2

|  | Mass of extract | Concentration of nepodin contained | Amount of nepodin contained |
|---|---|---|---|
| Crude Rumex plant root extract liquor | 1760 mg* | 5.3 wt % | 93.5 mg |
| Precipitate (3) | 128.4 mg | 22.7 wt % | 29.1 mg |

*The weight of the crude Rumex plant root extract liquor of R. obtusifolius was calculated by concentrating a portion of the solution.

Consequently, a high-nepodin-containing extract of Rumex plant root containing 22.7 wt % of nepodin was obtained as a final product.

Example 6: Evaluation of Extraction of Dried Product of Rumex Plant

Fifty grams of a dried root of Rumex plant (R. japonicus) that was produced by drying Rumex plant root at a lower temperature under vacuum was subjected to an extract treatment with 500 ml of 100% ethanol, 80% ethanol, or 60% ethanol at room temperature. The weight of extract as well as the content (%) and the amount (mg) of nepodin in the extract are shown in Table 3.

TABLE 3

| Ethanol concentration | Mass of Extract | Concentration of nepodin contained in extract | Amount of nepodin contained in extract |
|---|---|---|---|
| 100% ethanol | 610 mg | 15.2% | 92.6 mg |
| 80% ethanol | 9.9 g | 2.0% | 199 mg |
| 60% ethanol | 13.2 g | 0.3% | 37 mg |

As shown in Table 3, the content (%) of nepodin in the extract of the dried root of Rumex plant was higher for a higher concentration of ethanol.

Fifty grams of the root (wet) of Rumex plant was subjected to an extract treatment with 100% ethanol at room temperature, 40° C., 60° C., or 80° C. The weight of extract as well as the content (%) and the amount (mg) of nepodin in the extract are shown in Table 4.

TABLE 4

| Temperature | Mass of Extract | Concentration of nepodin contained in extract | Amount of nepodin contained in extract |
|---|---|---|---|
| room temperature | 1.36 g | 2.1% | 29 mg |
| 40° C. | 1.72 g | 1.9% | 33 mg |
| 60° C. | 1.72 g | 5.0% | 87 mg |
| 80° C. | 1.68 g | 0.7% | 12 mg |

As shown in Table 4, the content (%) of nepodin in the extract of the raw root of Rumex plant was higher at room temperature to 60° C.

Example 7: Production Method (2) for High-Nepodin-Containing Extract of Dried Root of Rumex Plant Five hundred grams of the root of Rumex plant (R. obtusifolius) was shredded using a garden shredder ("GS-2010," RYOBI). The shredded root was then dried with a hot air stream at 40° C. for 24 hours to obtain 100 g of the dried root of Rumex plant. To 1 L of ethanol, the dried root of Rumex plant was then added and the mixture was left to stand for 8 hours at room temperature to obtain a crude Rumex plant root extract. The resulting crude Rumex plant root extract was suction-filtered using a diaphragm pump and a filtration flask to obtain a crude Rumex plant root extract liquor.

500 mL of water was added to the crude Rumex plant root extract liquor and the solution was concentrated down to about 300 mL under reduced pressure to cause the solid component to precipitate. The precipitated solid component was separated and collected by centrifugation (7,500 rpm, 10 min).

The resulting solid component was added to 100 ml of a 0.1% (w/v) aqueous sodium bicarbonate solution and the mixture was stirred to obtain a suspension. The resulting suspension was separated by centrifugation (7,500 rpm, 10 min) into a supernatant (1) and a precipitate (1). The resulting precipitate (1) was added to 200 ml of a 0.1% (w/v) aqueous sodium hydroxide solution and the mixture was stirred. Subsequently, the mixture was separated by centrifugation (7,500 rpm, 10 min) into a supernatant (2) and a precipitate (2). To the resulting supernatant (2), a suitable amount of acetic acid was added with the aim of neutralization to cause the solid component to precipitate, followed by separation by centrifugation (7,500 rpm, 10 min) into a supernatant (3) and a precipitate (3). The resulting precipitate (3) was dried and the amount of the dried product of the precipitate (3) was determined to be 52 mg. The concentration of nepodin in the dried product of the precipitate (3) was 39.6 wt %. The results are shown in Table 5.

TABLE 5

|  | Concentration of nepodin contained | Amount of nepodin contained/Dry Mass of extract |
| --- | --- | --- |
| Crude Rumex plant root extract liquor | 10.6 wt % | 110 mg/1.04 g |
| Precipitate (3) | 39.6 wt % | 19.9 mg/52 mg |

*The weight of the crude Rumex plant root extract liquor of R. obtusifolius was calculated by concentrating a portion of the solution.

Consequently, a high-nepodin-containing extract of Rumex plant root containing 39.6 wt % of nepodin was obtained as a final product.

The other components in the high-nepodin-containing extract of Rumex plant root were identified: it turned out that the extract contained approximately 30% of fatty acid complexes, including a nepodin analog (8%; nakahalene) and anthraquinones (5%; emodin, chrysophanol, and physcion) as shown in the following formula (2).

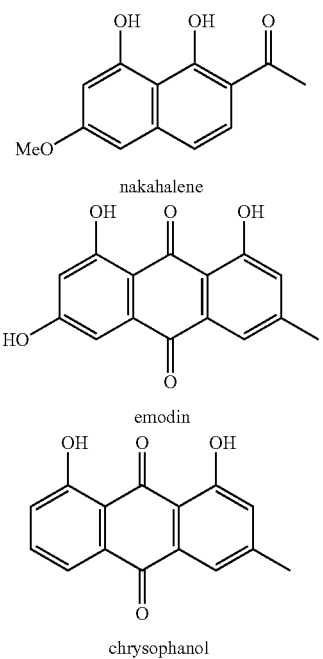

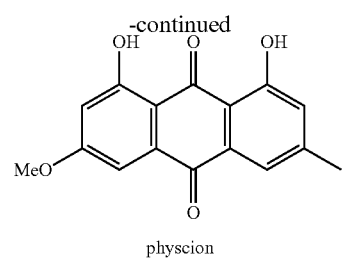

As has been described above, high-nepodin-containing extracts of Rumex plant roots were obtained by obtaining solid components of crude ethanol extracts of the Rumex plant roots by subjecting Rumex plant roots to extraction treatment with ethanol, and further treating the solid components with water, a weak alkali, a strong alkali and an acid. The resulting high-nepodin-containing extracts of Rumex plant roots contain a several times higher concentration of nepodin than any of the conventional crude ethanol extracts of Rumex plant roots, and are therefore useful as nepodin-containing products derived from natural materials and useful for producing nepodin in an economically advantageous fashion.

INDUSTRIAL APPLICABILITY

The present invention is useful in the fields of pharmaceutical products and quasi-pharmaceutical products. In particular, the invention is useful in producing active ingredients formulated in pharmaceutical products and quasi-pharmaceutical products for diseases the symptoms of which can be ameliorated by activating AMPK, such as glucose tolerance-improving agents, blood lipid level-lowering agents, and prophylactic and/or therapeutic agents for metabolic syndromes.

REFERENCE NUMERALS

10: Rumex plant root
11: Crude Rumex plant extract
12: Solid component of crude Rumex plant extract
13: Weak alkali insoluble product
14: Strong alkali soluble product
15: Nepodin-containing Rumex plant extract
20: Rumex plant residue
21: Liquid component of crude Rumex plant extract
22: Weak alkali soluble product
23: Strong alkali insoluble product
24: Neutralizing solution soluble product
30: Extraction treatment
31: Water-adding treatment/concentration treatment
32: Weak alkali treatment
33: Strong alkali treatment
34: Neutralizing treatment

The invention claimed is:
1. A method for producing a nepodin-containing Rumex plant extract, the method comprising the following steps (1) to (5):
   (1) a step of subjecting a Rumex plant to an extraction treatment using a nepodin-dissolving solvent to obtain a crude Rumex plant extract;
   (2) a step of subjecting the crude Rumex plant extract to a water-adding treatment and/or concentration treatment to obtain a solid crude Rumex plant extract;

(3) a step of subjecting the solid crude *Rumex* plant extract to a weak alkali treatment to obtain a weak alkali insoluble product;

(4) a step of subjecting the weak alkali insoluble product to a strong alkali treatment to obtain a strong alkali soluble product; and (5) a step of subjecting the strong alkali soluble product to a neutralization treatment to obtain the nepodin-containing *Rumex* plant extract.

2. The method for producing a nepodin-containing *Rumex* plant extract according to claim 1, wherein the nepodin-dissolving solvent is 20% to 100% (v/v) ethanol.

3. The method for producing a nepodin-containing *Rumex* plant extract according to claim 1, wherein the weak alkali treatment is a weak alkali treatment using a weak alkaline aqueous solution having a pH of 8 to 10.

4. The method for producing a nepodin-containing *Rumex* plant extract according to claim 1, wherein the weak alkali treatment is a weak alkali treatment using a weak alkaline aqueous solution obtained by mixing sodium bicarbonate and water, wherein the solution has a pH of 8 to 10.

5. The method for producing a nepodin-containing *Rumex* plant extract according to claim 1, wherein the strong alkali treatment is a strong alkali treatment using a strong alkaline aqueous solution having a pH of 12 to 14.

6. The method for producing a nepodin-containing *Rumex* plant extract according to claim 1, wherein the strong alkali treatment is a strong alkali treatment using a strong alkaline aqueous solution obtained by mixing sodium hydroxide and water, wherein the solution has a pH of 12 to 14.

7. The method for producing a nepodin-containing *Rumex* plant extract according to claim 1, wherein the neutralizing treatment is a neutralizing treatment using an acidic aqueous solution having a pH of 1 to 3.

8. The method for producing a nepodin-containing *Rumex* plant extract according to claim 1, wherein the neutralizing treatment is a neutralizing treatment using an acidic aqueous solution obtained by mixing water and an acid component selected from the group consisting of acetic acid and hydrochloric acid, wherein the solution has a pH of 1 to 3.

9. The method for producing a nepodin-containing *Rumex* plant extract according to claim 1, wherein the nepodin-containing *Rumex* plant extract is a nepodin-containing *Rumex* plant extract containing 20 wt % to 40 wt % of nepodin.

10. A nepodin-containing *Rumex* plant extract containing 20 wt % to 40 wt % nepodin and 60 wt % or less fatty acids obtained by the method according to claim 1.

11. The nepodin-containing *Rumex* plant extract according to claim 10, wherein the nepodin-dissolving solvent is 20% to 100% (v/v) ethanol.

12. The nepodin-containing *Rumex* plant extract according to claim 10, wherein the weak alkali treatment is a weak alkali treatment using a weak alkaline aqueous solution having a pH of 8 to 10.

13. The nepodin-containing *Rumex* plant extract according to claim 10, wherein the weak alkali treatment is a weak alkali treatment using a weak alkaline aqueous solution obtained by mixing sodium bicarbonate and water, wherein the solution has a pH of 8 to 10.

14. The nepodin-containing *Rumex* plant extract according to claim 10, wherein the strong alkali treatment is a strong alkali treatment using a strong alkaline aqueous solution having a pH of 12 to 14.

15. The nepodin-containing *Rumex* plant extract according to claim 10, wherein the strong alkali treatment is a strong alkali treatment using a strong alkaline aqueous solution obtained by mixing sodium hydroxide and water, wherein the solution has a pH of 12 to 14.

16. The nepodin-containing *Rumex* plant extract according to claim 10, wherein the neutralizing treatment is a neutralizing treatment using an acidic aqueous solution having a pH of 1 to 3.

17. The nepodin-containing *Rumex* plant extract according to claim 10, wherein the neutralizing treatment is a neutralizing treatment using an acidic aqueous solution obtained by mixing water and an acid component selected from the group consisting of acetic acid and hydrochloric acid, wherein the solution has a pH of 1 to 3.

18. The nepodin-containing *Rumex* plant extract according to claim 10, wherein the nepodin-containing *Rumex* plant extract is a nepodin-containing *Rumex* plant extract containing 20 wt % to 40 wt % of nepodin.

\* \* \* \* \*